United States Patent [19]

Blackbourn et al.

[11] Patent Number: 5,463,136
[45] Date of Patent: Oct. 31, 1995

[54] CUMENE HYDROPEROXIDE CLEAVAGE PROCESS

[75] Inventors: Robert L. Blackbourn, Houston; Edgar D. Allan, Katy; Loc B. Le; Snehal Patel, both of Houston, all of Tex.

[73] Assignee: Shell Oil Company, Houston, Tex.

[21] Appl. No.: 363,437

[22] Filed: Dec. 22, 1994

[51] Int. Cl.⁶ .................................................. C07C 37/08
[52] U.S. Cl. ............................................ 568/385; 568/798
[58] Field of Search .................................. 568/768, 798, 568/385

[56] References Cited

U.S. PATENT DOCUMENTS

| | | | |
|---|---|---|---|
| 2,757,209 | 7/1956 | Joris | 260/621 |
| 4,246,203 | 1/1981 | Wirth | 568/768 |
| 4,358,618 | 11/1982 | Sifniades et al. | 568/385 |
| 5,245,090 | 9/1993 | DeCaria et al. | 568/798 |
| 5,254,751 | 10/1993 | Zakoshansky | 568/798 |
| 5,371,305 | 12/1994 | Hood | 568/798 |

*Primary Examiner*—James H. Reamer
*Attorney, Agent, or Firm*—Todd F. Volyn

[57] ABSTRACT

A process for the decomposition of cumene hydroperoxide to phenol, acetone, and alpha-methylstyrene is presented. In this process, cumene hydroperoxide and sulfuric acid are reacted in a reflux cooled reactor the products of which are transported under inhibited conditions to a plug flow reactor, and are reacted to produce phenol, acetone, and alpha-methylstyrene. In one embodiment of the invention, a heat exchanger is used to obtain and maintain the inhibited conditions of the transported reactor products.

18 Claims, 1 Drawing Sheet

CUMENE HYDROPEROXIDE CLEAVAGE PROCESS

FIELD OF THE INVENTION

This invention relates to the production of phenol, acetone, and α-methyl styrene by the cleavage of cumene hydroperoxide. Background of the Invention Phenol, acetone (dimethyl ketone or "DMK"), and α-methyl styrene (AMS) can be manufactured by the acid-catalyzed cleavage of cumene hydroperoxide (CHP). This CHP decomposition is very exothermic, typically yielding nearly 60 Kcal/mole of CHP. The reaction is nearly stoichiometric under severe conditions with the production of phenol and acetone in the presence of whatever solvent may be present and a small amount of other materials. Only a small amount of CHP is generally left unreacted.

CHP is the oxidation product of cumene. During the oxidation of cumene small amounts of dimethyl phenyl carbinol (DMPC) and acetophenone are also produced. It is this DMPC which can be readily converted to AMS. Unfortunately, the AMS can dimerize or react with phenol to form cumyl phenols (Cps) under severe conditions. This results in disappointingly low AMS yields.

U.S. Pat. No. 2,757,209 to Joris proposed a two stage process to reduce dimers and cumylphenols. CHP is decomposed in a back-mixed reactor in the presence of sulfur dioxide catalyst in the first stage. The reactors useful in such processes are externally cooled/pump circulated. The reaction products of the first stage are then heated and introduced into a plug flow reactor in order to dehydrate the DMPC to AMS. U.S. Pat. No. 4,016,213 to Yeh proposes the treatment of the reaction product of the back-mixed reactor with base and DMPC. Crude phenol is recovered through separation.

U.S. Pat. No. 4,358,618 to Sifniades recognized that during the production of phenol and DMK, CHP and DMPC can condense to form dicumyl peroxide (DCP). This DCP was found to be an intermediate which can be used to form phenol, DMK, AMS and some of the AMS dimers and other yield reducing byproducts. Sifniades proposed controlling the formation of DCP by increasing the concentration of CHP in the reactor. This would favor the reaction of DMPC and CHP to DCP as opposed to the formation of dimers and cumyl phenols from DMPC. The reaction products of this reactor would then be given residence time in a plug flow reactor/zone in order to promote further decomposition of CHP (to below 0.4% w) to phenol and DMK. Finally, the reaction products from the plug flow reactor/zone would be further reacted under harsh conditions in another plug flow reactor to produce phenol, DMK, and AMS from the acid catalyzed DCP decomposition.

U.S. Pat. No. 5,254,751 to Zakoshansky proposed a staged CHP decomposition process. The initial CHP decomposition reaction is carried out in a multiplicity of sequential reactors in a non-isothermal manner, with a higher acid concentration than that of Snifiades and is conducted in the presence of excess DMK. An ammonia co-catalyst is added to the reactor products prior to their introduction into a plug flow reaction zone. The reactor products are then introduced into a plug-flow reactor to decompose the DCP to phenol, acetone, and AMS.

U.S. Pat. No. 5,245,090 to DeCaria proposed the use of a reflux cooled (boiling) reactor in the first stage of the CHP decomposition process followed by a second stage hydrogenator/reactor. As in U.S. Pat. No. 4,358,618, mild reaction conditions promoting formation of DCP are employed. The product of the first reaction stage is fed to a second stage packed bed reactor which contains a hydrogenation catalyst (operated at about 100 psig hydrogen pressure under harsher conditions than the first stage). The small amount of AMS generated by the dehydration of DMPC in the first stage is mainly converted to cumene. The DCP formed in the first stage reactor is then decomposed to yield phenol, DMK, and AMS. The AMS formed in this stage is also hydrogenated to cumene with some being recycled back to the first stage.

Thus, the art has taken two different approaches to the problem of CHP cleavage. One-step processes attempt to react CHP to products all at once leading to the unavoidable production of yield loss byproducts. Staged processes, on the other hand, rely on leaving some CHP unreacted in the first reactor to take advantage of the DCP mechanism.

Employing the staged method of Snifiades involves the use of an externally cooled, pump circulated reactor. In addition to added capital for the pumping system, one pays a price in terms of energy consumption and design freedom with such systems. With respect to energy consumption, a liquid circulation system requires some minimum amount of pumped circulation to both maximize the heat transfer coefficient (to minimize heat transfer area) and minimize temperature rise so that the reaction temperature can be controlled at the best operating point. The energy used in this circulation adds nothing to the process and could be as much as 1.3 Hp/ton CHP processed.

With respect to design freedoms, a liquid circulated/looped reactor system must balance reactor cooling area, circulation rate, reactor residence time, and temperature differential requirements in a fixed area/volume design. Additionally, inherent operating safety is a concern with these externally cooled systems. In the event of local power or pump failure the circulated system heat removal capability falls to near zero as no circulation flow results in a very low heat transfer capability.

A system without such energy consumption, design freedom, and safety deficiencies would be advantageous in CHP production. A reflux cooled (boiling) reactor is one such reactor. These reactors allow the products to boil and use the heat of vaporization to subsequently cool the reactor and maintain it in its proper operating conditions. No external cooling or pumping of coolant is used. In relying on gravity runback flow from elevated condensers, the reactors would continue to function at normal heat removal capabilities even in the event of a local power failure. Moreover, cooling needs are discrete and separate from residence time and temperature considerations. Therefore this system enjoys additional freedom in operating condition selection not found in externally cooled systems.

If one were to use the Sifniades method of passing on the reactor products (which contain 0.5 to 5% wt CHP) to an intermediate plug-flow zone the kinetically fast and very exothermic CHP decomposition reaction would continue and with the attendant problem of DMK boiling. This would introduce vapor in the product stream making pumping the products to the next stage of the reaction physically difficult and extremely dangerous.

Except as set forth in U.S. Pat. No. 5,245,090, reflux cooled reactors have not been used in multistage cumene hydroperoxide cleavage processes. That process is a cleavage/hydrogenation process. The first stage products are moved to a high pressure fixed bed noble metal on carbon hydrogenator/reactor where the bulk of AMS generated in both stages is directly converted to cumene for distillation and recycle.

The art could greatly benefit from a combination of suitable reactor type and reaction conditions so that reactions favoring the production of products and useful intermediates such as DCP could be passed to subsequent treatment without the need for undue residence time in numerous reaction zones. Such processes could be conducted more safely given the exothermic mixture of reactor products and the conditions under which they come into contact.

SUMMARY OF THE INVENTION

In this invention a process for the decomposition of cumene hydroperoxide to phenol, DMK, and AMS is presented. In this process, cumene hydroperoxide and sulfuric acid are reacted in a reflux cooled reactor the products of which are transported under inhibited reaction conditions to a plug flow reactor, and are reacted to produce phenol, DMK, and AMS.

In one embodiment of the invention, a heat exchanger is used to obtain and maintain the inhibited reaction conditions.

In another embodiment of the invention, reaction severity inhibitors such as water and/or DMK are added to the transported reactor products to obtain and maintain the inhibited reaction conditions of the transported reactor products.

DETAILED DESCRIPTION OF THE INVENTION

It has now been found possible to achieve highly selective and productive yields of phenol, DMK, and AMS through the staged cleavage of CHP using a reflux cooled (boiling) reactor. In this process, CHP and DMBA are first reacted under the appropriately mild conditions necessary to prevent the production of yield loss byproducts. CHP is reacted to near completion in the reflux cooled reactor. The products of the reflux cooled reactor are then reacted in a plug flow reactor for finishing. Before this occurs, however, the reactor products are inhibited from undergoing significant further reaction so that they may be safely and effectively transported.

As used throughout this specification, the following terms shall have the prescribed meanings: "Reaction inhibition" and like terms mean positive steps taken to essentially prevent the further reaction of reflux cooled reactor products. While it is desirable to completely stop the further reaction of these products, reaction inhibition such that not more than about 1% wt (based on weight of total reflux cooled reactor products) of CHP further react is acceptable. "Severity inhibitor" means an agent or agents which reduce the total effective acidity of the solution comprising the reflux cooled reactor products.

Figure 1:
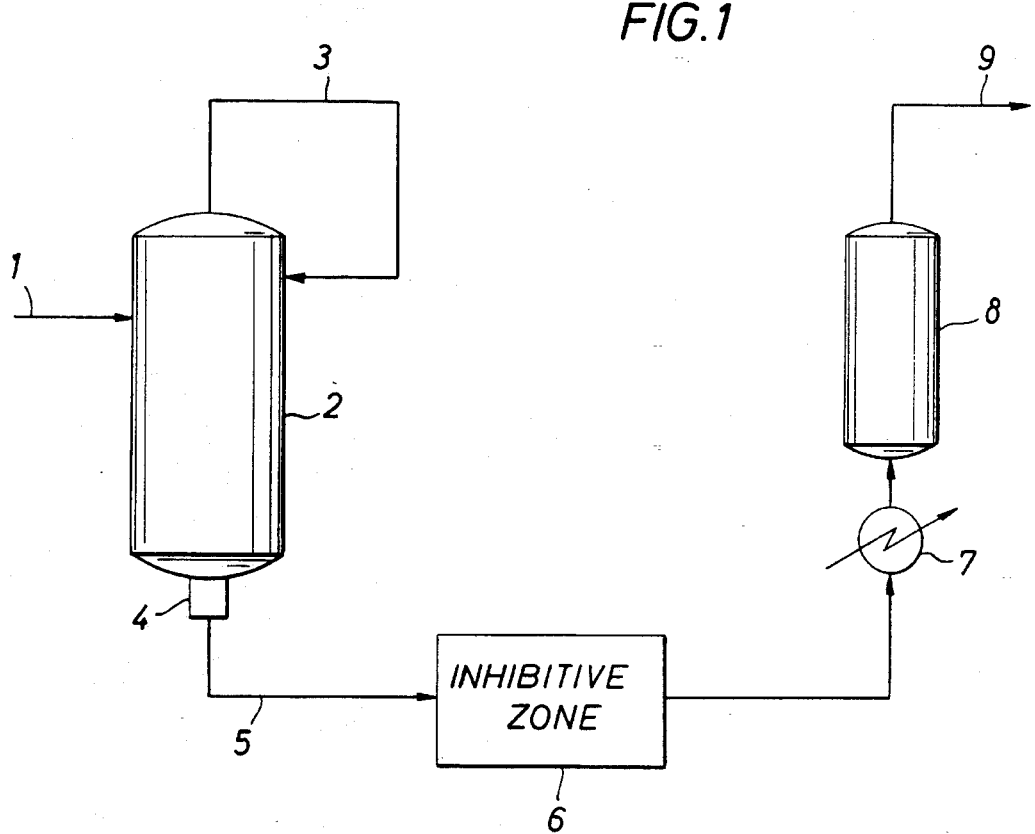
FIG. 1 is a schematic illustration of a process according to this invention.

Turning now to the drawings, FIG. 1 is a schematic representation of a process according to this invention. Feed, 1 comprising between about 82 and 88% wt CHP, between about 3.5 and 5.0% wt DMPC, between about 0.5 and 1.0% wt acetophenone (AP), about 0.10 to about 0.30% wt DCP, and the remainder cumene enters the reflux cooled reactor, 2 along with between about 50 and 300 ppmw (based on weight of CHP) $H_2SO_4$, about 0.5% wt water (based on weight of CHP), between about 2 and 20% wt of added DMK (based on weight of feed). The reactor is maintained at temperatures between about 70° and about 90° C. by regulation of a vacuum applied to the system.

As the contents of the reflux cooled reactor are reacted in reflux cooled reactor, 2 they are brought to a boil. Vaporized reaction products rise through reflux line, 3 and condense as they move along the line. Eventually, the condensed products are returned to the reactor. Movement of the condensate occurs through the force of gravity. In this way, the heat of vaporization and subsequent condensation remove heat from the reactor and maintain its operation in the proper temperature range without the use of external pumps, compressors, added energy or the like. This contributes to energy efficiency, safety, and design freedom not found in externally cooled systems.

The reaction conditions within the reflux cooled reactor 2 are significantly milder than those of one step processes especially with respect to acid concentration. This favors the reaction of CHP and DMBA to form DCP which is eventually fully reacted to form AMS, phenol, and DMK. Thus, the reflux cooled reactor products leaving the reactor at exit point 4 comprise between about 0.5% and 3.0% wt CHP. This insures that the CHP and DMBA reaction to DCP takes place and that only a very small percentage of AMS derived heavy ends are manufactured.

Reflux cooled reactor products are transported through reactor exit point 4 through transport line(s) 5. A pump 6b is used to facilitate this movement of product mix to subsequent stages of the process.

Since the reflux cooled reactor is operated so that its contents are boiled for heat removal and the reaction involved is highly exothermic, the reflux cooled reactor products will leave the reactor exit point 4 at or very near boiling conditions with unreacted CHP present. This could present a problem if the exothermic CHP decomposition were allowed to proceed unchecked in the transport line 5. That is, the CHP could easily heat the material to its bubble point, overcoming the associated head pressure of the system (created by the liquid level of the reactor versus the height of pump 6a). Any trace of vapor thus formed in the transfer line would cavitate the pump and therefore cause a general failure of the process.

Figure 2:
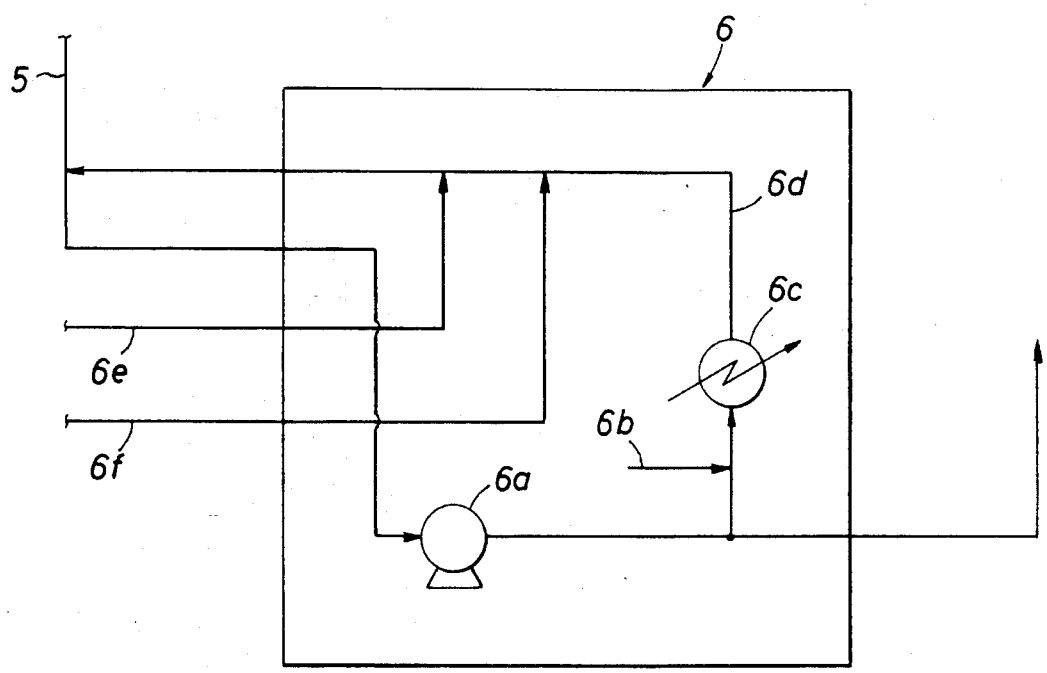
FIG. 2 is a schematic illustration of an embodiment of the inhibitive zone used to obtain and maintain the inhibited reaction conditions of the transported reactor products.

These problems are avoided by inhibiting the reaction of reflux cooled reactor products in the transport line(s) 5. This can be accomplished under isothermal conditions or under conditions in which there is a loss of heat accompanying the transportation of reflux cooled reactor products to the plug flow reactor. This is affected through the establishment of an inhibitive zone 6, an embodiment of which is shown in detail in FIG. 2. Temperature control is the preferred means of reaction inhibition within the inhibitive zone.

Reactor products leaving the pump proceed along the transport line until they reach the recirculation line inlet 6b. At this point, between about 20% and 40% of the products flowing through the line are diverted via a three-way control valve or similar device. The diverted products then pass through a heat exchanger 6c. This heat exchanger can be any commercially available heat exchanger capable of handling such products. This can be, for example, a simple shell and tube heat exchanger. The heat exchanger typically cools the products flowing therethrough by between about 20° and 60° F. However, it will be appreciated by those skilled in the art that this amount of heat transfer can be adjusted so that the products are retained in an inhibited state as they are transported. This can be further ensured through the adjustment of heat exchanger operations by any of the well known electronic or mechanical control means connected to any number of thermocouples along the transport line.

Desired temperatures within the inhibitive zone can also depend on the relative position of the reflux cooled reactor with respect to the pump. When the reflux cooled reactor liquid level is equal to the pump height, reaction inhibition is attained through the maintenance of the temperature of products at the entry to the pump and kept equal to or less than the temperature of the products at the exit point 4. If the pump is lowered in elevation compared to the liquid level of the reflux cooled reactor, the temperature requirement can be relaxed according to the amount of head pressure generated by the positioning as will be appreciated by one skilled in the art. Nevertheless, it is preferred that the temperature of products at the entry to the pump are kept equal to or less than the temperature of the products at the exit point 4.

Cooled, recirculated reflux reactor products then continue through the recirculation line outlet 6d and are ultimately mixed with reflux reactor products as they leave the reactor exit point 4 or at a point proximate to the exit point.

Other means for inhibiting the subsequent reaction of products exiting the reflux cooled reactor include the addition of a severity inhibitor to the reactor products. Reduced temperature and the reduction of effective acidity both serve to quench or inhibit the CHP reaction. Severity inhibitors include, for example, water and/or DMK. While either or both can be added to the transported product stream anywhere between the exit point 4 and the pump 6, it is preferred that any such addition be made at a point between the recirculation line outlet 6d and the point at which recirculated reflux cooled reactor products are mixed with fresh reactor products.

Water is the preferred severity inhibitor as it improves throughput. Additionally, overall energy consumption (distillation and recycle of DMK) and the production of the byproduct hydroxy acetone (acetol) and other unwanted ketones are all minimized with the use of water. Acetol is a known color body precursor in the production of other potential downstream products. DMK is the preferred severity inhibitor when emphasis is placed on obtaining the highest AMS recovery for a given quantity of acid.

In the case of water addition, enough water is typically added to the water that is produced during the reaction to bring the total quantity of water to between about 0.5% wt and 2.0% wt (based on weight of total reflux cooled reactor products). It is preferred that the amount of water not exceed 3% wt (based on the weight of the total reflux cooled reactor products). The temperature of the additional added water is between about 25° and 70° C.

In the case of DMK addition, between about 2% wt and 20% wt (based on weight of total reflux cooled reactor products) are typically added at temperatures below the boiling point of acetone under the given reduced pressure conditions.

Again, one skilled in the art will readily appreciate the adjustments needed to reduce the reactivity to a point consistent with the operation of the invention. DMK and water are readily available from condensate and current DMK recycle lines. It is further possible to regulate the conditions in the reflux cooled reactor by adding these same ranges of severity inhibitor thereto.

In the most preferred embodiment of this invention, the inhibitive zone functions solely through the operation of a heat exchanger to inhibit reaction in the transport lines. Between about 20 and 40% of the reflux cooled reactor product stream is diverted through this heat exchanger prior to recirculation back into the transport line. Between about 0.5 and 2.0% wt water is added to the reflux cooled reactor with between about 50 and 300 ppmw acid therein. The reactants are given between about 10 and 20 minutes residence time in the reflux cooled reactor and between about 0.5 and 3.0% wt CHP is left unreacted in the reflux cooled reactor.

Reflux cooled reactor products which were not diverted to the recirculation line inlet 6b continue so that the reaction to products can be finished in plug flow reactor 8. The conditions needed to complete this reaction at good yields are harsh. That is, the reactor utilizes high temperatures to drive the DCP and any remaining CHP to AMS, DMK, and phenol. Typically, these conditions include temperatures between about 110° and 150° C. and $H_2SO_4$ concentrations between about 50 and 300 ppmw with residence times between about 60 and 180 seconds.

Care must be taken to stop the reaction in the plug flow reactor by first cooling and then neutralizing the reaction product at or near a point of maximum yield recovery. This is readily determined by measuring the amount of heavy ends formed relative to the amount of phenol present. Simple, well known High Performance Liquid Chromatography (HPLC) analysis and/or Gas Chromatography (GC) analysis can be used to determine the heavy component formation and phenol production to this end.

Achieving these conditions, is greatly aided by the use of a heater 7 to heat the reflux cooled reactor products prior to their entry into the plug flow reactor. Once products leave the plug flow reactor they can be further processed/separated according to methods well known in the art.

The invention will now be further illustrated by the following nonlimiting examples.

EXAMPLES

In each of the examples a continuous lab scale reflux cooled reactor having a volume of about 250 ml. was employed. The reactor was equipped with an acetone condenser. A large syringe pump was used to continuously feed the reflux cooled reactor with the CHP feed and any additional acetone. A smaller syringe pump was used to meter in acid and any water additions. Temperature of the reactor was controlled by regulating the vacuum applied to the system. A length of jacketed ⅛ inch stainless steel tubing served as the transfer line from the reflux cooled reactor to the transfer pump. Water circulated from a bath was used to keep the material inside the tubing isothermal and thereby provided an inhibitive zone. The temperature on the interior of the transfer line (inhibitive zone) was maintained at less than the boiling point of the reaction mixture at the pressure in which each example was operated. The material was then either sent directly to a high surface area product cooler during one stage operation (comparative examples), or to a length of jacketed ⅛" stainless steel tubing which served as a second stage plug flow reactor (ca. 1.5 minute residence time, with a 10 minute first stage residence time).

A feed of 125 ml. was used (fed at a rate of about 12.5 ml. per minute) in each example. The CHP feed was obtained from Aldrich Chemical Company, Inc. All examples used CHP from the same lot. It contained about 83.83 % W CHP, 7.69% W DMPC, 1.31% W AP, 0.79% w DCP, remainder cumene. This material is known to contain much more DMPC, AP, and DCP than is typically produced in industrial processes.

A ratio of heavy components divided by the amount of phenol produced (HE/P) is reported as a measure of the yield. The components of the heavy ends were DMBA, AMSDs, cumylphenols, and DCP. AP was excluded from the list because it did not participate or form during the course of the reaction under the conditions employed. All examples were run to a point at which the final CHP concentration was at or below 0.05% W (essentially, totally reacted).

Example 1 (Staged Cleavage of CHP with Inhibitive Zone)

A staged CHP cleavage process was conducted as set forth immediately above. First stage conditions were as follows: 200 ppmw acid; 0.5% W added water (1.48% W total); 75° C., 10 minute residence time; and 2.5% W added acetone. The second stage reactor had a 1.5 minute residence time. When the plug flow reactor was run at a temperature of 127° C. an HE/P ratio of 0.0695 was obtained.

Example 2 (Additional DMK)

The process similar to that of Example 1 was conducted with additional acetone present in the feed. The first stage conditions included 200 ppmw acid, 0.1% W added water (0.94% W total); 75° C.; 10 minute residence time; and 20% W added acetone. The residence time in the second stage reactor was 1.5 minutes. An HE/P ratio of 0.0643 was obtained when the plug flow reactor was operated at about 120° C.

Example 3 (Low Acid Concentration)

A process similar to that of Example 1 was conducted with the following parameters. The first stage conditions included 75 ppmw acid, 0.5% W added water (0.94% W total); 80° C.; 10 minute residence time; and 2.5% W added acetone. The residence time in the second stage reactor was 1.5 minutes. An HE/P ratio of 0.0695 was obtained when the plug flow reactor was operated at about 150° C.

Example 4 (High Acid Concentration)

A process similar to that of Example 1 was conducted with the following parameters. The first stage conditions included 300 ppmw acid, 0.5% W added water (1.46% W total); 80° C.; 10 minute residence time; and 2.5% W added acetone. The residence time in the second stage reactor was 1.5 minutes. An HE/P ratio of 0.071 was obtained when the reactor was operated at about 120° C.

Example 5 (Single Stage Process)(Not According to the Invention)

A single stage process was conducted so that the reaction was completed in the reflux cooled reactor without subsequent reaction in a plug flow reactor.

The reflux cooled reactor was operated under the following conditions: 1200 ppmw acid (based on CHP in feed); 0.5% W added water (1.48% W total); 80° C., 10 minute residence time, and no added acetone. The HE/P ratio was determined to be 0.1028.

We claim as our invention

1. A process for the decomposition of cumene hydroperoxide to phenol, acetone, and alphamethylstyrene comprising:

reacting cumene hydroperoxide and sulfuric acid in a reflux cooled reactor, transporting the reaction products of the reflux cooled reactor under inhibited conditions to a plug flow reactor, reacting the reaction products of the reflux cooled reactor in the plug flow reactor to produce phenol, acetone, and alpha-methylstyrene, and recovering a member of the group consisting of phenol, acetone, alpha-methylstyrene, and mixtures thereof.

2. The process of claim 1 wherein said transportation step is isothermal.

3. The process of claim 1 wherein said transportation step is accompanied by a loss of heat.

4. The process of claim 1 wherein said transportation step occurs through an inhibitive zone.

5. The process of claim 4 wherein said inhibitive zone comprises a heat exchanger.

6. The process of claim 4 wherein a portion of said reflux cooled reactor products are transported through said heat exchanger and then recirculated into the reflux cooled reactor product being transported from said reflux cooled reactor before entering said plug flow reactor.

7. The process of claim 6 wherein said recirculated products of said reflux cooled reactor are recirculated to a point proximate to the exit point of said reflux cooled reactor.

8. The process of claim 6 further comprising the step of adding a severity inhibitor to said reflux cooled reactor products.

9. The process of claim 8 wherein said severity inhibitor comprises water.

10. The process of claim 9 wherein up to about 3% wt (based on weight of total reflux cooled reactor products) water is added to said reflux cooled reactor products.

11. The process of claim 8 wherein said severity inhibitor comprises acetone.

12. The process of claim 11 wherein up to 20% wt (based on total reflux cooled reactor products) acetone is added to said reflux cooled reactor products.

13. The process of claim 1 wherein a pump assists the transport of said reflux cooled reactor products to said plug flow reactor.

14. The process of claim 13 wherein the temperature of said reflux cooled reactor products at said pump is less than or equal to the temperature of the exit point of the reflux cooled reactor.

15. The process of claim 1 further comprising the step of adding water to said reflux cooled reactor.

16. The process of claim 15 wherein up to about 3% wt (based on total reflux cooled reactor products) of water is added to said reflux cooled reactor.

17. The process of claim 1 further comprising the step of adding acetone to said reflux cooled reactor.

18. The process of claim 17 wherein up to about 20% wt (based on total reflux cooled reactor products) of acetone is added to said reflux cooled reactor.

* * * * *